US00PP34261P2

(12) United States Plant Patent
Werner et al.

(10) Patent No.: US PP34,261 P2
(45) Date of Patent: May 24, 2022

(54) PEACH PLANT NAMED 'NCPEACH-6'

(50) Latin Name: *Prunus persica*
Varietal Denomination: NCPeach-6

(71) Applicant: North Carolina State University, Raleigh, NC (US)

(72) Inventors: Dennis Werner, Raleigh, NC (US); Leanne M. Kenealy, Durham, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 17/346,449

(22) Filed: Jun. 14, 2021

(51) Int. Cl.
*A01H 5/00* (2018.01)
*A01H 6/74* (2018.01)

(52) U.S. Cl.
USPC ..... Plt./156

(58) Field of Classification Search
USPC ..... Plt./156
See application file for complete search history.

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

A new and distinct cultivar of ornamental peach plant, referred to by its variety name, 'NCPeach-6', is disclosed. The new cultivar forms double red-colored flowers. Dark purple-colored foliage is exhibited. Moderately slow, dwarf and globose growth habit is displayed. The new variety is well suited for providing attractive ornamentation in the landscape.

3 Drawing Sheets

Latin name of genus and species of plant claimed: *Prunus persica.*

Variety denomination: 'NCPeach-6'.

BACKGROUND OF THE INVENTION

The present invention relates to a new and distinct cultivar of ornamental peach plant botanically known as *Prunus persica* and hereinafter referred to by the cultivar name 'NCPeach-6'.

The new cultivar originated in a controlled breeding program in Raleigh, N.C. in March 2013.

The new ornamental peach cultivar is the result of a controlled cross. The female (seed) parent of the new cultivar is *Prunus persica* 'Bonfire', not patented, characterized by its single pink-colored flowers, purple-colored foliage, and dwarf growth habit. The male (pollen) parent of the new cultivar is *Prunus* 'NCSU Double Red Dwarf', not patented, characterized by its double red-colored flowers, green-colored foliage, and dwarf growth habit. The new cultivar was discovered and selected as a single seedling within the second-generation progeny of the above-stated controlled cross. The plant was selected for its double red-colored flowers, purple-colored foliage, and dwarf growth habit in March 2017 in a controlled environment in Raleigh, N.C.

Asexual reproduction of the new cultivar by chip budding since August 2017 in Belvidere, Tenn. has demonstrated that the new cultivar reproduces true to type with all of the characteristics, as herein described, firmly fixed and retained through successive generations of such asexual propagation.

The first offer for sale/sale of the new variety was Jan. 4, 2021 by the inventor or another who obtained the new variety directly or indirectly from the inventor.

SUMMARY OF THE INVENTION

The following characteristics of the new cultivar have been repeatedly observed and can be used to distinguish 'NCPeach-6' as a new and distinct cultivar of ornamental peach plant:

1. Double red-colored flowers;
2. Dark purple-colored foliage; and
3. Moderately slow, dwarf and globose growth habit.

The new variety of the present invention can readily be distinguished from its ancestors. More specifically, plants of the new cultivar plants display double red-colored flowers, whereas plants of 'Bonfire' (i.e., the seed parent) display single pink-colored flowers. Plants of the new cultivar provide purple-colored foliage, whereas plants of 'NCSU Double Red Dwarf' (i.e., the pollen parent) provide green-colored foliage.

Of the many commercially available *Prunus* cultivars, the most similar in comparison to the new cultivar is 'Bonanza', not patented. However, plants of the new cultivar differ from plants of 'Bonanza' in at least the following characteristics:

1. Plants of the new cultivar have darker colored flowers than plants of 'Bonanza'.
2. Plants of the new cultivar have dark purple-colored foliage, whereas plants of 'Bonanza' have green-colored foliage.

BRIEF DESCRIPTION OF THE PHOTOGRAPHS

The accompanying photographs show, as nearly true as it is reasonably possible to make the same in color illustrations of this type, typical habit and foliage characteristics of the new cultivar. Colors in the photographs differ slightly from the color values cited in the detailed description, which accurately describes the colors of 'NCPeach-6'. The plants were chip budded and were approximately one-year old and peach seedling understock was used. Photos were taken in August 2018 in Belvidere, Tenn.

DETAILED BOTANICAL DESCRIPTION

Figure 1:
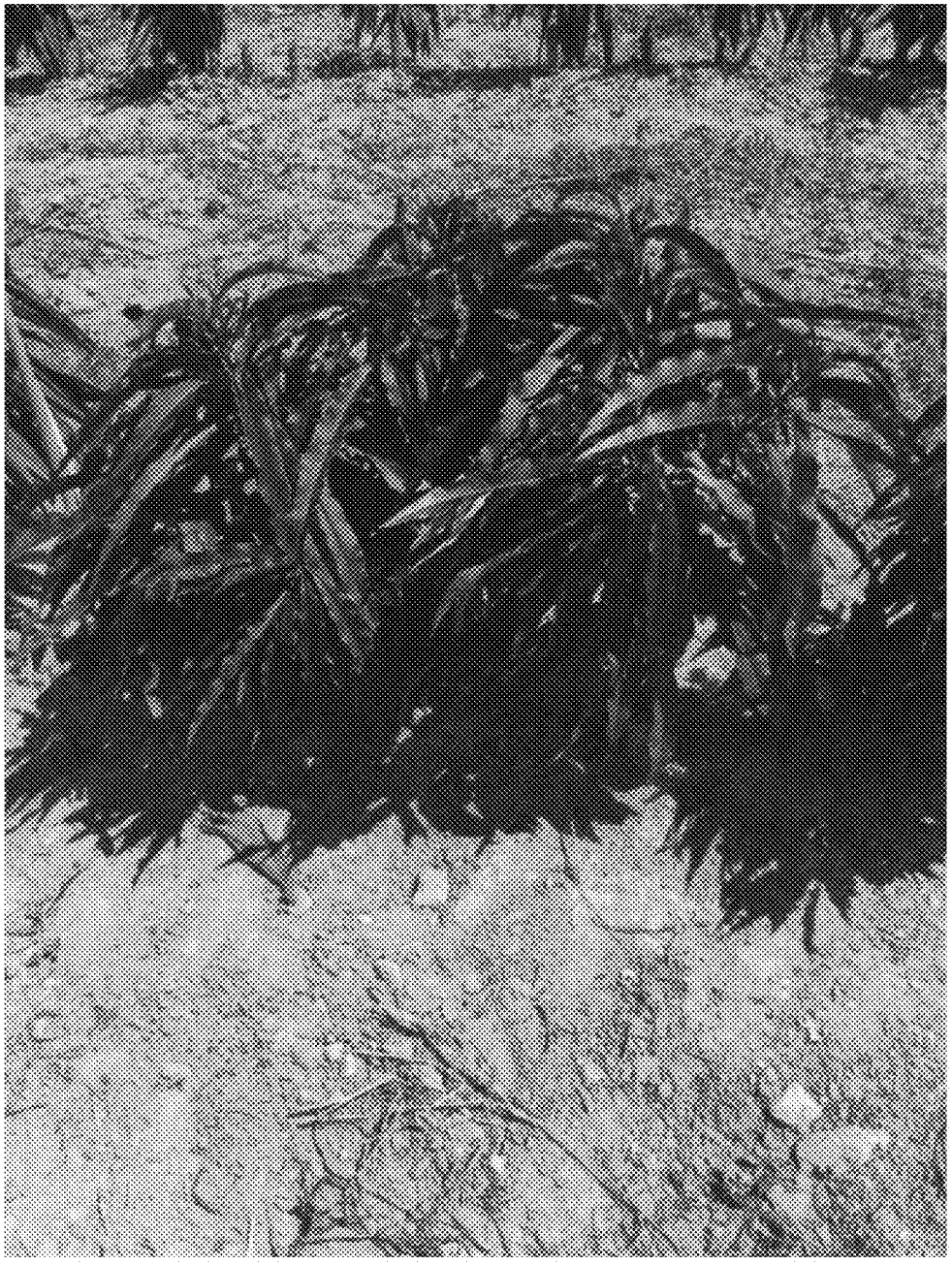
FIG. 1 illustrates a side view of 'NCPeach-6' growing in the ground.
Figure 2:
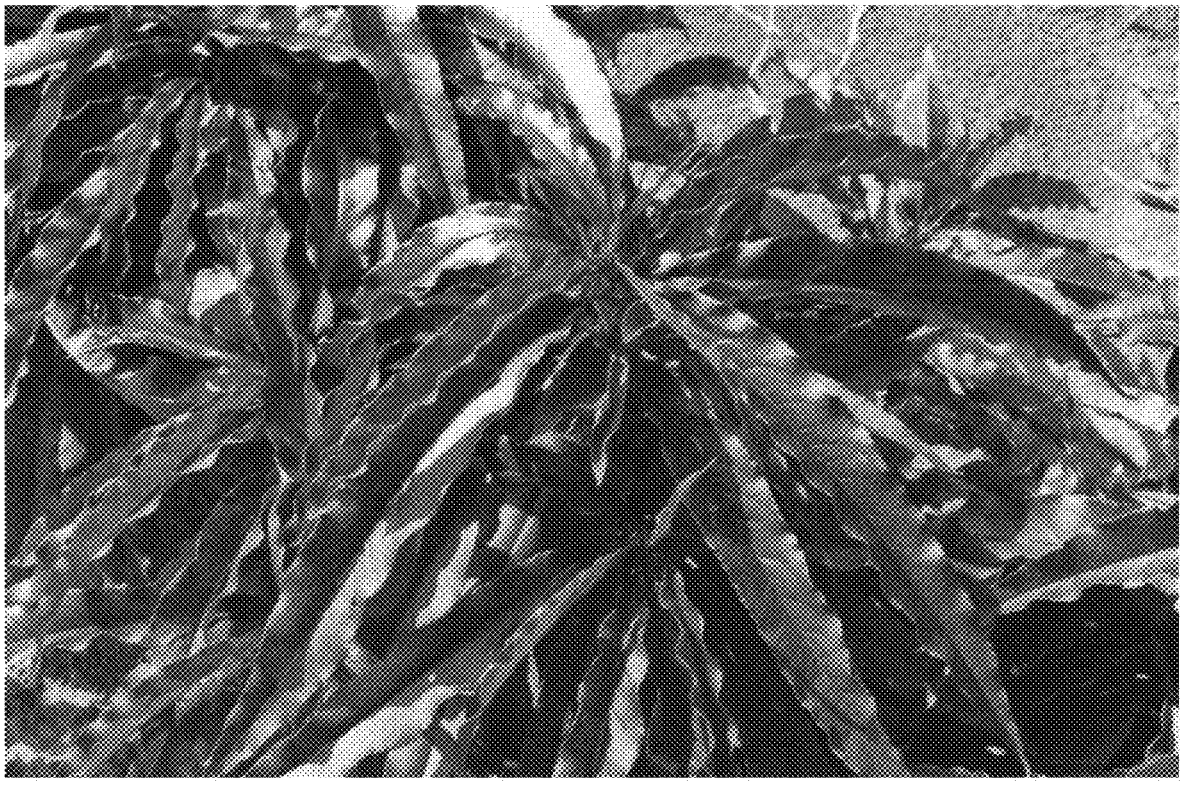
FIG. 2 illustrates a close-up view of the foliage of 'NCPeach-6'.
Figure 3:
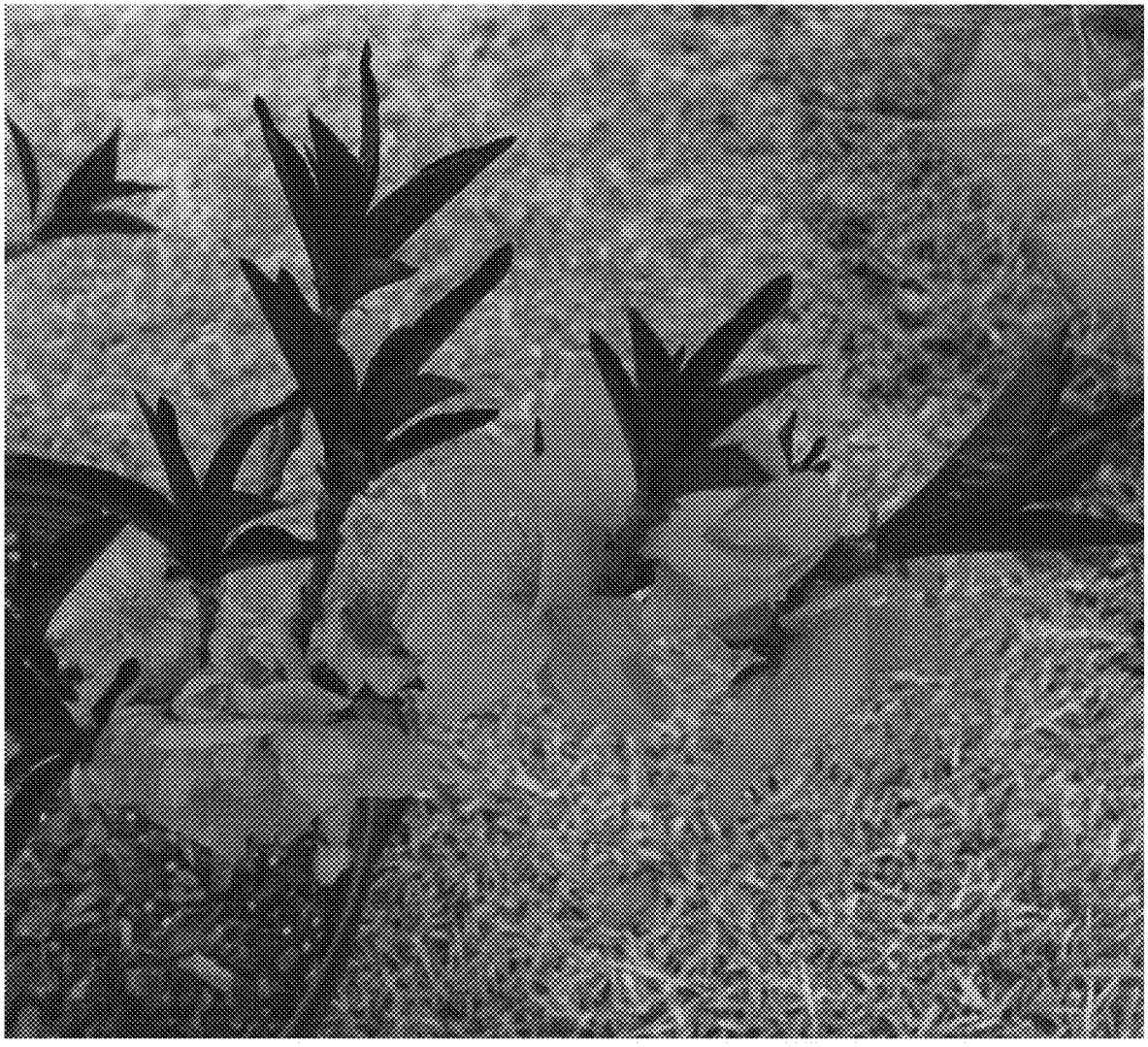
FIG. 3 illustrates a close-up view of the flowers of 'NCPeach-6'.

The chart used in the identification of colors described herein is The R.H.S. Colour Chart of The Royal Horticultural Society, London, England, 2007 edition, except where general color terms of ordinary significance are used. The terminology which precedes reference to the chart has been added to indicate the corresponding color in more common terms. The color values were determined in 2019 under natural light conditions in Raleigh, N.C.

The following descriptions and measurements describe the original seedling plant growing outside in Raleigh, N.C. Plants were approximately three years of age. Measurements and numerical values represent averages of typical plants.

Botanical classification: *Prunus persica* cultivar NCPeach-6.

Parentage:

*Female parent.*—*Prunus* 'Bonfire', not patented.

*Male parent.*—*Prunus* 'NCSU Double Red Dwarf', not patented.

Propagation:

*Type*.—Chip budding.

Plant description:

*Type*.—Deciduous perennial tree.

*Growth habit and general appearance*.—Moderately slow, dwarf and semi-globose.

*Commercial crop time*.—Approximately 12 months to finish from planting budded rootstock (peach seedling understock) into a 3-gallon container.

*Hardiness*.—Hardy to USDA Zone 7b.

*Disease and pest resistance*.—Plants of the new variety have not been noted to be resistant to pathogens and pests common to *Prunus*.

*Size*.—Height: Approximately 45.0 cm. Width: Approximately 44.0 cm.

*Trunk*.—Diameter: Approximately 2.0 cm. Texture: Slightly rugose. Color: Commonly near Brown Group N200B.

*Branches*.—Highly branched. Strength: Moderately strong. Shape: Circular. Diameter of one-year old shoots: Approximately 5.0 mm. Length of one-year old shoots: Approximately 6.5 cm. Internode length of one-year old dormant shoots: 1.0-1.5 mm. Stem Texture: Rough. Color of one-year old stems: Commonly near Brown Group 200B. Lenticel: Numerous, small. Lenticel length: Less than 1.0 to 2.0 mm. Lenticel shape: Slightly elongate. Lenticel color: Commonly near Grey Group 201C.

*Trunk*.—Bark surface: Slightly rugose. Color: Commonly near Brown Group N200B.

Foliage description:

*General description*.—Type: Deciduous. Arrangement: Alternate.

*Leaves*.—Shape: Elliptic. Apex: Acuminate. Base: Tapered. Margin: Weakly serrate. Margin undulation: moderate. Length: Approximately 12.0 cm. Width: Approximately 2.7 cm. Texture of upper and lower surfaces: Smooth, glabrous. Venation pattern: Brachidodromous. Color of upper surface of young foliage: Commonly near Purple Group N77A. Color of lower surface of young foliage: Commonly near Red-Purple Group 59A. Color of upper surface of mature foliage: Commonly near Purple Group N77A fading to near Violet-Blue Group N92A, eventually fading to Yellow-Green Group 147A. Color of under surface of mature foliage: Commonly near Greyed-Purple Group 183B with venation of near Red-Purple Group 60A. Fragrance: None detected.

*Petiole*.—Length: Approximately 1.0 mm. Diameter: Approximately 1.0 mm. Texture: Smooth, glabrous. Color: Commonly near Purple Group N77A.

Flowering description:

*Flowering season*.—Flowers in late winter to early spring.

*General description*.—Single perfect flower with bilateral symmetry. Aspect: Facing outward. Quantity per plant: Approximately 100.

Flower description:

*General description*.—Type: Single, rosaceous, not persistent. Aspect: Outward. Fragrance: unknown.

*Bud just before opening*.—Shape: Round. Diameter: Approximately 6.0 mm. Length: Approximately 6.0 mm. Color: Commonly near Red-Purple Group 58B. Texture: Tomentose.

*Corolla*.—Diameter: Approximately 3.6 cm. Depth: Approximately 1.0 cm.

*Petals*.—Quantity: 15 on average, unfused. Shape: Orbicular. Margin: Entire. Apex: Rounded. Base: Obtuse. Length: Approximately 9.0 mm. Width: Approximately 8.0 mm. Texture of upper and lower surfaces: Glabrous. Color of upper and lower surfaces when first and fully open: Commonly near Red-Purple Group N74C.

*Calyx*.—Shape: vase-shaped. Diameter: Approximately 3.0 mm. Length: Approximately 5.0 mm. Color of outer and inner surfaces: Commonly near Purple Group 59A. Texture of outer and inner surfaces: Glabrous.

*Sepals*.—Quantity: 8 on average, fused at the base. Color of adaxial and abaxial surfaces: Commonly near Purple Group 59A. Texture of adaxial and abaxial surfaces: Glabrous.

*Pedicel*.—Strength: Strong. Shape: Round. Length: Approximately 5.8 mm. Diameter: Less than 1.0 mm. Texture: Glabrous. Color: Commonly near Yellow-Green Group 144C.

*Reproductive organs*.—Androecium: Stamen quantity per flower: 30 on average, unfused. Stamen length: Approximately 9.0 mm on average. Stamen width: Less than 1.0 mm. Filament length: Less than 1.0 mm. Filament color: commonly near Red-Purple Group 59A. Anther shape: Round. Anther length: Less than 1.0 mm. Anther width: Less than 1.0 mm. Anther color: Commonly near Red-Purple Group 59A. Pollen amount: Abundant. Pollen color: Commonly near Yellow Group 13A. Gynoecium: Pistil quantity: 1 per flower. Pistil length: Approximately 1.0 mm on average. Pistil width: Less than 1.0 mm. Pistil texture: Glabrous. Stigma shape: Round. Stigma color: Commonly near Green Group 143AA. Stigma length: Less than 1.0 mm. Stigma width:

Less than 1.0 mm. Style shape: Elongate. Style length: Approximately 0.7 mm. Style width: Less than 1.0 mm. Style color: Commonly near Red-Purple Group 73A. Ovary position: Superior. Ovary shape: Round. Ovary width: Approximately 1.0 mm. Ovary color: Commonly near Red-Purple Group 72A. Ovary texture: Pubescent.

*Fruit*.—Shape: Slightly elongate. Color: Commonly near Yellow-Green Group 151A to Orange-Red Group N30B. Flesh Color: Commonly near Green-Yellow Group 1D. Length: Approximately 4.2 cm. Width: Approximately 3.4 cm. Seed coat color: Commonly near Greyed-Orange Group N167B.

The new cultivar has not been observed under all possible environmental conditions to date. Accordingly, it is possible that the phenotype may vary somewhat with variations in the environment, such as temperature, light intensity, and day length, without, however, any variance in genotype.

I claim:

1. A new and distinct variety of Ornamental Peach plant named 'NCPeach-6' characterized by the following combination of characteristics:

(a) forms double red-colored flowers;

(b) exhibits dark purple-colored foliage; and (c) provides moderately slow, dwarf and globose growth habit;

substantially as herein shown and described.

* * * * *